US00PP17044P3

(12) United States Plant Patent
Westendorp

(10) Patent No.: US PP17,044 P3
(45) Date of Patent: Aug. 22, 2006

(54) *HOSTA* PLANT NAMED 'INDEPENDENCE'

(50) Latin Name: *Hosta hybrid*
Varietal Denomination: Independence

(75) Inventor: Jeffrey A. Westendorp, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 10/849,720

(22) Filed: May 20, 2004

(65) Prior Publication Data

US 2005/0262609 P1 Nov. 24, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent Bell
*Assistant Examiner*—Louanne Krawczewicz Myers

(57) ABSTRACT

A new and distinct *Hosta* plant named 'Independence' characterized by very thick substance in the leaves, deep green coloring, upright habit in youth, lavender flowers held nicely above foliage, wide creamy-white margin, and the margin containing numerous small green flecks suitable for landscape, potted culture, or cut flower arrangements.

2 Drawing Sheets

Botanical classification: *Hosta* hybrid (Tratt.).
Variety denomination: 'Independence'.

SUMMARY, BACKGROUND AND ORIGIN OF THE PLANT

The new and distinct *Hosta* cultivar 'Independence', hereinafter also referred to as 'Independence' and "the plant" is a new and distinct plant. It was found by Jeff A. Westendorp in 1999 as an un-induced whole plant sport of the *Hosta* cultivar 'Revolution' (not patented) growing in a greenhouse in a nursery in Zeeland, Mich., USA. The plant has been successfully propagated by tissue culture and division methods at the same nursery to produce identical plants that maintain the unique characteristics of the original plant. The plant is stable and reproduces true to type in successive generations of asexual reproduction.

*Hosta* 'Independence' differs from its parent sport, 'Revolution', in that the color pattern is completely reversed in the leaf. 'Revolution' has the white center with green speckling within and a dark green margin. 'Independence' has a white margin with the green speckling within and a green center. The most similar known *hosta* cultivar is 'Lakeside Zinger' which has the same color pattern as 'Independence' but the margin is much wider on 'Independence'. The new plant is also about twice the size in total habit and leaf dimensions, and the thickness of the leaf of 'Independence' from top to bottom surface is much greater.

BRIEF DESCRIPTION OF THE DRAWINGS

The photographs of the new plant demonstrate the overall appearance of the plant, including the unique traits. The colors are as accurate as reasonably possible with color reproduction. Ambient light spectrum, source and direction may cause the appearance of minor variation in color.

GENERAL DESCRIPTION OF THE PLANT

Figure 1:
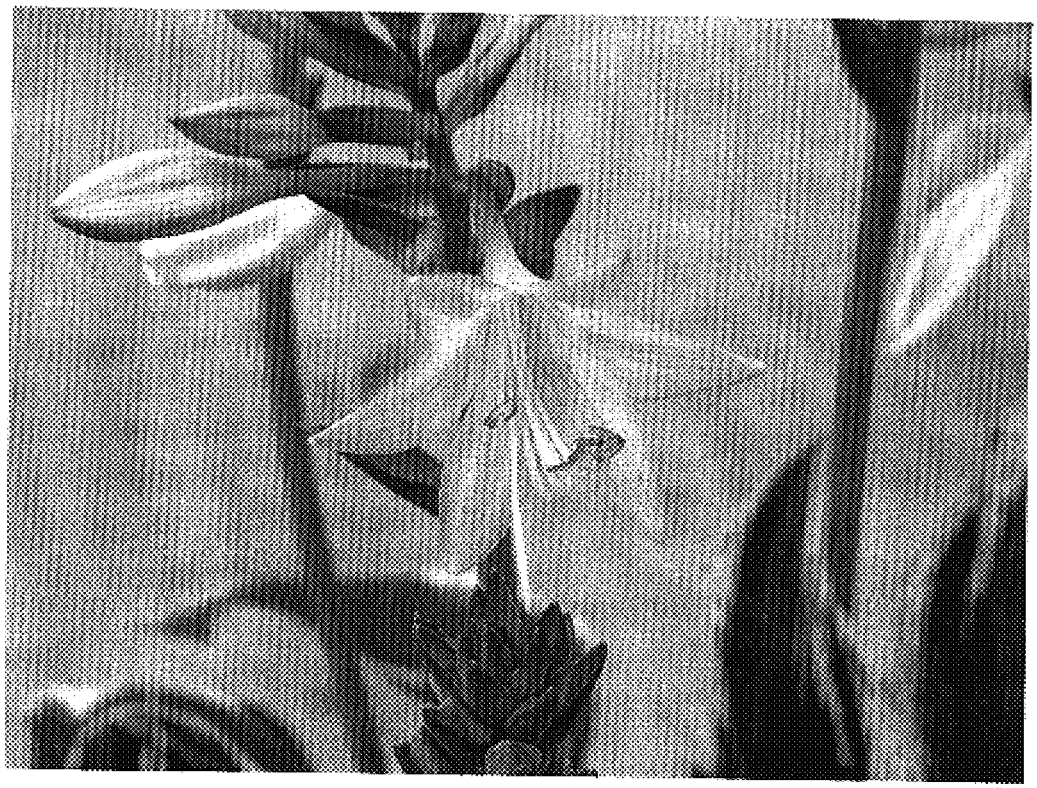
FIG. 1 shows a close-up of the flowers of the plant.
Figure 2:
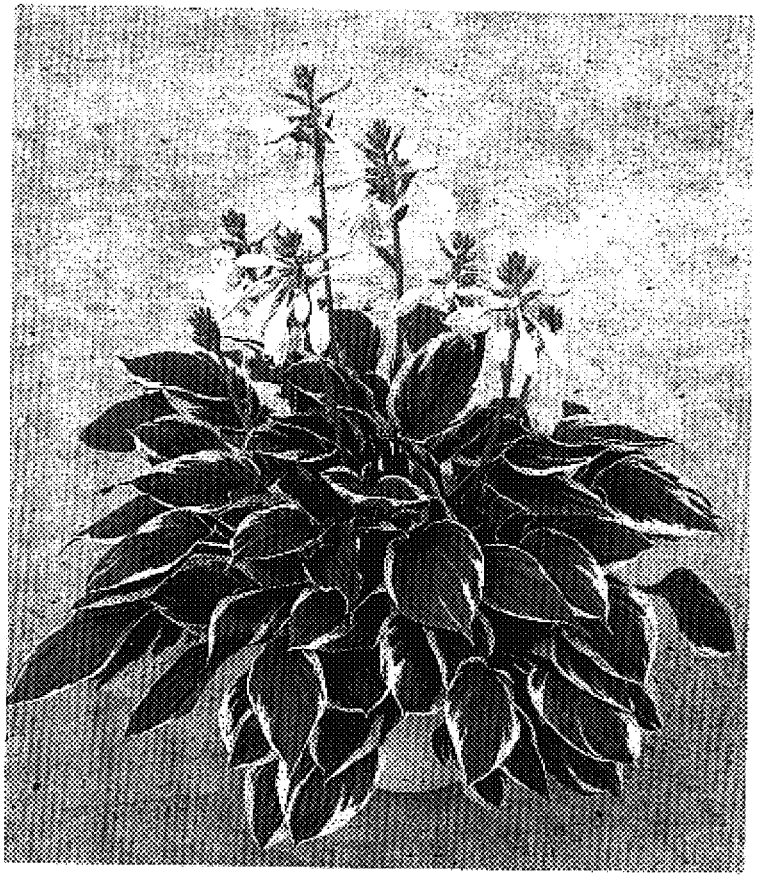
FIG. 2 shows the overall plant.
Figure 3:
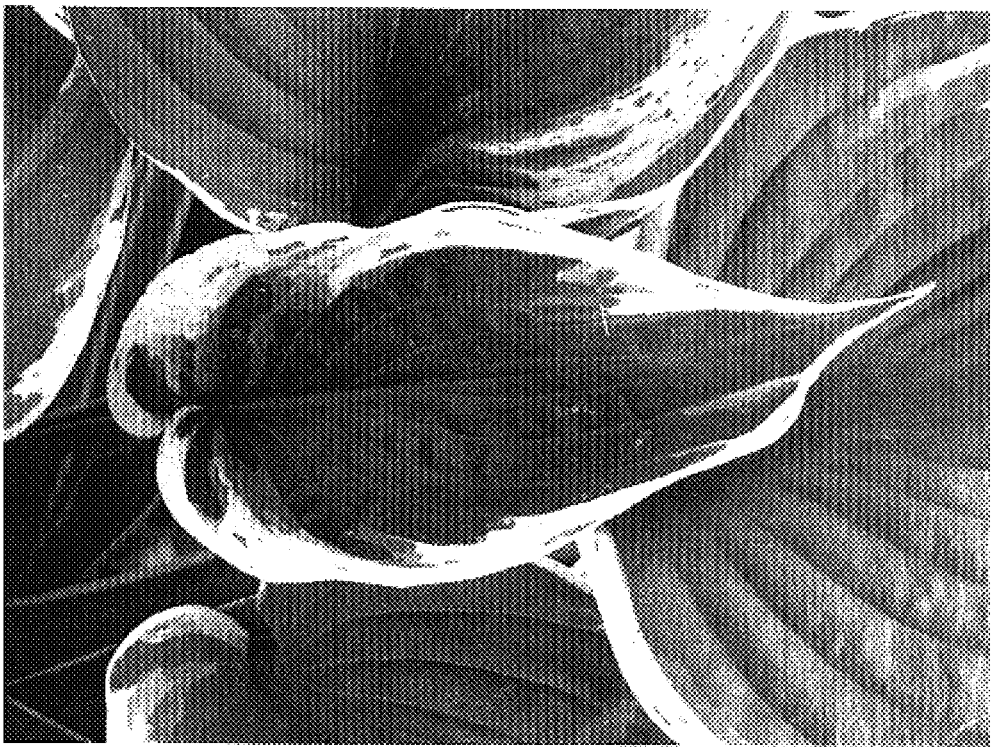
FIG. 3 shows a close-up of the leaf with unique variegation in early season.
Figure 4:
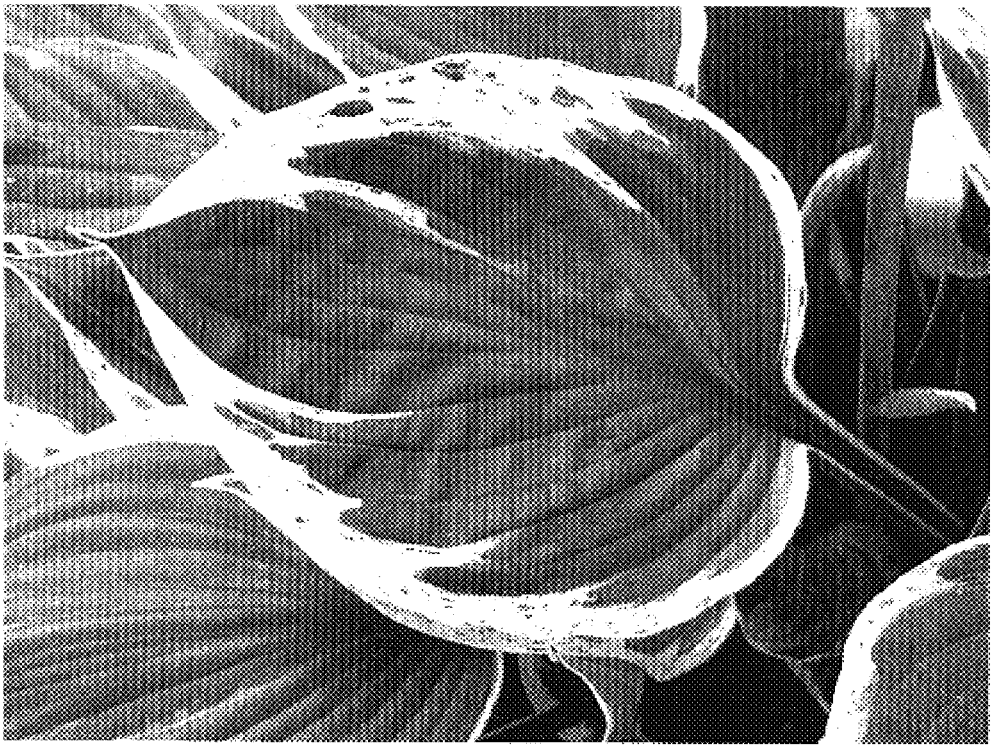
FIG. 4 shows the leaf later in the season.

The genus *Hosta* is mainly native to Japan with a few species originating from China and Korea. There are over 3,300 cultivars registered with The American *Hosta* Society, which is the International Cultivar Registration Authority for the genus *Hosta*. *Hosta* 'Independence' differs from all of these in that it has:

1. Very thick substance in the leaves
2. Deep green coloring
3. Upright habit in youth
4. Wide creamy white leaf margins
5. The margins contain numerous green flecks of various sizes
6. Light lavender flowers.

DETAILED BOTANICAL DESCRIPTION

The following descriptions and color references are based on the 2001 edition of The Royal Horticultural Society Colour Chart except where common dictionary terms are used. The new plant, *Hosta* 'Independence', has not been observed under all possible environments. The phenotype may vary slightly with different environmental conditions, such as temperature, light, fertility, moisture and maturity levels, but without any change in the genotype. The following observations and size descriptions are of a two-year old plant in a two-gallon container grown in Zeeland, Mich., USA under 50% shade on cloudless days, day temperatures of 18 to 28 degrees C., and night temperatures of 15 to 20 degrees C.

Botanical classification: *Hosta* hybrid cultivar 'Independence'.

Parentage: Naturally occurring sport of *Hosta* 'Revolution' (not patented).

Propagation:

*Method.*—By tissue culture and division.

*Time to initiate roots from both division and tissue culture.*—Three to four weeks.

*Rooting habit.*—Normal, fleshy, lightly branching.

Plant description:

*Plant shape and habit.*—Hardy herbaceous perennial with basal rosette leaves, symmetrical, upright and erect through flowering period; more horizontal in older plants.

*Crop time.*—Under normal growing conditions about 22 weeks to finish in a one-liter container. Plant vigor is good to high.

*Plant size.*—Foliage height at flowering is 25 to 33 cm tall from soil line to the top of the leaves and 23 to 28 cm wide.

Foliage description:

*Shape and size.*—Ovate to broadly ovate leaf blades have an acute apex and cordate base. The leaf blades are 18 to 22 cm long and 10 to 12 cm wide. The leaf blade margin is entire and the variegation pattern on the edge varies in different regions of the leaf from 10 to 25 mm wide.

*Texture, both surfaces.*—Glabrous.

*Blade color.*—Center portion adaxial surface of young emerging leaves is a deep green closest to RHS 141 A. Later in the growing season, the center adaxial surface is between RHS 139 A and RHS 136 A. The adaxial margin surface is RHS 11 B to RHS 11 C on young leaves, and whiter than RHS 155 D on leaves later in the season. The abaxial center color is RHS 137 A. The abaxial margin color is nearly identical to the adaxial surface color throughout the seasons. There are also three or more intermediate color patterns between the center and the margin. The most prominent intermediate color bands on the adaxial surface are yellow-green RHS N138 C and RHS 143 B. Other more yellow, lighter, or more grayed bands are also sometimes present in thinner and shorter stripes. The main intermediate band visible on the abaxial side is RHS 144 C on young leaves with little change over the season. The green flecks visible on the adaxial side in the margin are variable and range from RHS 136 A to RHS 138 A and the same color on the abaxial side.

*Veins.*—Parallel, lightly impressed, color on top and bottom of leaf identical to surrounding variegation.

*Petioles.*—16 to 20 cm long and 15 mm wide. The 1 to 2 mm wide margin starts RHS 11 B and lightens to RHS 11 D, but varies like the leaves depending on how much light the petiole receives. The center of the petiole is green RHS 136 A on both surfaces.

Flower description:

*Buds.*—Two days prior to opening violet RHS 84 C; 6 to 7 cm long, up to 1.5 cm wide, clavate with acute apex and longer thin base.

*Flowers.*—15 to 21 per scape; 1 scape per plant division; funnelform; 4 to 6 cm wide and 6 to 8 cm long, (distal flowers being smaller), persists for a normal period, up to two days on or cut from plant, and the scapes remain effective from mid July to late August; No detectable fragrance.

*Bract.*—Sessile with acute apex; margin entire; up to 5 cm long and 2 cm wide, smaller near apex; Bract color for both upper and lower surfaces with the same central color as the leaf blades and the 1 to 2 mm wide margin closest to RHS N74 B, rarely cream-colored, RHS 11 C.

*Peduncle.*—Typically one per mature division; erect to 70 cm tall and to 1 cm in diameter, green color RHS N138 C with the glaucous surface; RHS 136 B with surface removed.

*Pedicel.*—Approximately 1 cm long, 3 mm wide, RHS N78 C to RHS N78 D.

*Tepal.*—Six fused at the base; clavate with acute apex; entire; approximately 7 cm long and 1.2 cm wide; arranged in two layers of three, the inner three with clear 1 to 2 mm margin; center adaxial surface, or inside, color of tepals red purple RHS 69D with three violet stripes of RHS N78 D. Abaxial surface is a uniform RHS 84 D, except for the clear margin, and with slightly darker veins but no noticeable stripes.

*Gynoecium.*—Single; Style — 5 to 6 cm long, white, 1 mm diameter, curled at distal end.

*Stigma.*—2 mm to 3 mm in diameter, white.

*Androecium.*—Filaments — six, white, approximately 1 mm in diameter and to 5 cm long.

*Anthers.*—5 to 6 mm long, 1.5 mm wide, about RHS 83 A around margin of abaxial side, white in center, pollen is yellow-orange RHS 17 B.

*Fruit.*—Pods to 5 cm long and 10 to 12 mm in diameter, variable in color similar to the peduncles with flecks of reddish pigment RHS 59 B proportional to the amount of sunlight. Seeds are single winged dark brown drupe about RHS 200 A to RHS N200 A, 12 to 15 mm long and 3 to 4 mm wide.

Disease resistance: The plant is more tolerant of direct sun, and resists scorching of the light margin more than most other varieties. The plant is more resistant to slugs and most pests common to *hostas* than cultivars with *Hosta plantaginea* in the parentage, but resistance beyond those *hostas* of the Fortunei Group (those of similar genetic relationship) has not been observed. It grows best with plenty of moisture and adequate drainage, but is able to tolerate some drought. Hardiness and other disease resistance are typical of other *hostas,* at least from USDA zone 3 through 9.

I claim:

1. A new and distinct cultivar of ornamental *Hosta* plant named 'Independence' as herein described and illustrated, with unique green speckles on a cream-colored margin, suitable as a potted plant, for the garden, and for cut flower arrangements.

* * * * *